(12) United States Patent
Lobedann et al.

(10) Patent No.: US 11,786,615 B2
(45) Date of Patent: Oct. 17, 2023

(54) UNIT OPERATION AND USE THEREOF

(71) Applicant: Bayer Aktiengesellschaft, Leverkusen (DE)

(72) Inventors: Martin Lobedann, Cologne (DE); Laura David, Buesingen (DE); Sven-Oliver Borchert, Berlin (DE); Lisa Marie Waldschmidt, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 507 days.

(21) Appl. No.: 16/772,068

(22) PCT Filed: Sep. 18, 2018

(86) PCT No.: PCT/EP2018/075164
§ 371 (c)(1),
(2) Date: Jun. 11, 2020

(87) PCT Pub. No.: WO2019/063357
PCT Pub. Date: Apr. 4, 2019

(65) Prior Publication Data
US 2021/0069359 A1    Mar. 11, 2021

(30) Foreign Application Priority Data

Dec. 13, 2017 (EP) .................................... 17206952
Dec. 20, 2017 (EP) .................................... 17208952

(51) Int. Cl.
*A61L 2/00* (2006.01)
*B01D 15/00* (2006.01)
(Continued)

(52) U.S. Cl.
CPC .......... *A61L 2/0088* (2013.01); *A61L 2/0094* (2013.01); *A61L 2/18* (2013.01); *B01J 19/0006* (2013.01);
(Continued)

(58) Field of Classification Search
CPC .. A61L 2/0082; A61L 2/0088; A61L 2202/21; A61L 2202/15; C02F 1/52
(Continued)

(56) References Cited

U.S. PATENT DOCUMENTS 7,420,183 B2   9/2008   Kaiser et al.
7,651,660 B2   1/2010   Kaiser et al.
(Continued)

FOREIGN PATENT DOCUMENTS

EP    1339643 B1    1/2008
EP    1914202 A1    4/2008
(Continued)

OTHER PUBLICATIONS

PCT International Search Report for PCT/EP2018/075164, dated Nov. 26, 2018.

*Primary Examiner* — Monzer R Chorbaji
(74) *Attorney, Agent, or Firm* — McBee Moore & Vanik, IP, LLC

(57) ABSTRACT

The invention provides a unit operation formed by a device and its use for continuous virus inactivation of a continuous flow of a process fluid. The unit operation formed by a device comprises a single inlet at one end and an outlet at the opposite end and at least one HFI, characterized in that the HFI further comprises at least one installation.

9 Claims, 2 Drawing Sheets

(51) Int. Cl.
*B01D 17/06* (2006.01)
*A61L 2/18* (2006.01)
*B01J 19/00* (2006.01)
*C12N 7/06* (2006.01)
*A61L 101/46* (2006.01)

(52) U.S. Cl.
CPC ......... *B01J 19/006* (2013.01); *B01J 19/0066* (2013.01); *C12N 7/06* (2013.01); *A61L 2101/46* (2020.08); *A61L 2202/14* (2013.01); *A61L 2202/21* (2013.01); *A61L 2202/22* (2013.01); *B01J 2219/00033* (2013.01); *B01J 2219/00042* (2013.01); *C12N 2760/00063* (2013.01)

(58) Field of Classification Search
USPC .............. 422/292, 300; 210/198.1, 787, 749, 210/748.11

See application file for complete search history.

(56) References Cited

U.S. PATENT DOCUMENTS

| | | | |
|---|---|---|---|
| 7,695,675 | B2 | 4/2010 | Kaiser et al. |
| 10,022,463 | B2 | 7/2018 | Lobedann et al. |
| 2002/0096648 | A1 | 7/2002 | Kaiser et al. |
| 2003/0049809 | A1 | 3/2003 | Kaiser et al. |
| 2004/0248076 | A1 | 12/2004 | Kaiser et al. |
| 2007/0003430 | A1 | 1/2007 | Kaiser et al. |
| 2010/0314325 | A1* | 12/2010 | Lean ...................... C02F 1/5281 210/219 |
| 2016/0375159 | A1* | 12/2016 | Lobedann ............. A61L 2/0088 422/28 |

FOREIGN PATENT DOCUMENTS

| | | |
|---|---|---|
| EP | 1916224 A1 | 4/2008 |
| EP | 1464342 B1 | 10/2009 |
| EP | 2261178 A1 | 12/2010 |
| WO | 0174407 A1 | 10/2001 |
| WO | 0238191 A2 | 5/2002 |
| WO | 2013020775 A2 | 2/2013 |
| WO | 2015135844 A1 | 9/2015 |
| WO | 2017096490 A1 | 6/2017 |

* cited by examiner

UNIT OPERATION AND USE THEREOF

CROSS-REFERENCE TO RELATED APPLICATIONS

This application is the National Stage entry of International Application No. PCT/EP2018/075164, filed 18 Sep. 2018, which claims priority to European Patent Application No. 17208952.6, filed 20 Dec. 2017 and European Patent Application No. 17206952.8, filed 13 Dec. 2017.

BACKGROUND

Field

The present invention relates to a unit operation formed by a device, in particular a virus-inactivation device, and a use thereof.

Description of Related Art

Biopharmaceutical production processes typically need to involve at least one step of virus inactivation. For a product to be safe, the production process must inactivate (or remove) a sufficient amount of present virus particles. A common technique for inactivating (enveloped) viruses is acidifying a product solution or contacting a product with an acidic medium. Virus inactivation at low pH in batch mode is frequently employed in the biopharmaceutical production of physiologically active agents, such as antibodies. The product to be inactivated is in this case generally a liquid that potentially contains active virus particles. A solution of the product is transferred into a suitable container, adjusted to a pH of ≤4 by means of an acidic solution, homogenized if required, and left to rest for the time needed. At inactivated pH value the viruses are inactivated if exposed to the pH over a certain product- and process-dependent time. Under these conditions the entire content of the container is exposed to inactivation for approximately the same residence time, so that the reduction in virus load achieved is essentially the same in any fluid portion within the container.

A further common technique for inactivating viruses enveloped in a lipid coat, especially in the blood plasma industry, is the solvent/detergent (S/D) inactivation. A solvent and a detergent are added to the product in order to interrupt the lipid coating of viruses. Subsequently the solvent and the detergent need to be removed from the product. A solution of the product is transferred into a suitable container, solvent and detergent added, and the solution is left to rest for the time needed. Again, the entire content of the container is exposed to inactivation for approximately the same residence time.

Where a process for the production of a biopharmaceutical and/or biological product, e.g. a pharmaceutical antibody, is to be run in continuous operation mode, providing the same situation is a challenge. Continuous flow requires an alternative to an incubation in a distinct container, however, a common pipe does not allow for a unique holding time for any given fluid portion within the pipe, since laminar flow in a pipe has a parabolic velocity profile, resulting in a broad residence time distribution. Below a minimum incubation time at low pH no effective inactivation of viruses is achieved, whereas extended incubation time at low pH can damage a biological macromolecule product such as a protein. Therefore it is essential to achieve a narrow residence time distribution for the conditions of low pH. This cannot be achieved by means of turbulent mixing, since a turbulent flow involves high flow velocities. The resulting shear forces bear a high risk of damage to a biological macromolecule product such as a protein. Additionally if the long residence time such as 60-120 min of a common viral inactivation is to be carried out at a low pH, a disadvantageously large production plant is needed.

One way of carrying out continuous virus inactivation is irradiation with UV-C light: WO2002038191, EP1339643B1, EP1464342B1, EP1914202A1 and EP1916224A1 describe the use of a helical residence loop in which the material to be inactivated is irradiated with UV-C light and the viruses present are consequently inactivated. When a fluid flows through a helically coiled tube, centrifugal force acts on the fluid. The centrifugal forces induce secondary flows known as Dean vortices which leads to improved radial mixing and thus more homogeneous irradiation of the material to be inactivated. The helix structure used in the sources mentioned is a straight helical coil without changes in direction of the axis of the helix.

Another application in the process for the production of a pharmaceutical and/or biological product requiring a distinct holding time is the precipitation or crystallization of small macromolecules.

Helical coils are widely used in heat and mass exchangers. They can also be used in production processes for improving the mixing efficiency under laminar flow conditions. At low Dean numbers, the use of a helical coil is, nevertheless, not sufficient to achieve sufficient mixing for obtaining a narrow residence time distribution.

International patent application WO 2015/135844 discloses a suitable way of addressing the need to provide a process operated under continuous flow with a defined range of a holding time for virus inactivation. The process of WO 2015/135844 involves the use of a coiled flow inverter (CFI), for example in the form of a plurality of coils linked by bends at a certain angle, typically in the range from 45° to 180°. A narrow residence time distribution is achieved that allows a sufficient virus inactivation at a defined product-dependent and process-dependent minimal residence time. The bends rearrange the secondary flow patterns, leading to improved radial mixing. Mixing efficiency increases with an increase in Dean number and with the number of bends. At a given minimum residence time needed for sufficient viral inactivation, the process minimizes the maximum residence time that would lead to product damage.

SUMMARY

The inventors have, however, found that upscaling of a device with a coiled flow inverter, which involves increasing tubing diameters, poses difficulties, since larger conduits are more difficult to purge than tubing with small diameters. In particular, de-airing of helices that are oriented at an angle relative to the direction of gravitation can be slow and tedious as each turn of an inclined helix has an upper point where air bubbles can accumulate.

DETAILED DESCRIPTION OF A PREFERRED EMBODIMENT

The present inventors have found that the principle of flow inversion through bends is not the only way of increasing mixing effects of a helical tube, and that effective mixing can also be achieved by means of an installation. As used herein the term "installation" refers to a device for mixing fluids that does not require an actuated element, but achieves mixing by making use of fluid mechanics Thus, an installation is characterized by at least one of a plurality of geometric elements contained in a cylindrical conduit or squared housing, by branchings and junctions of a cylindrical conduit involving a plurality of channels and/or by a contraction such as an injector or a nozzle. The plurality of geometric elements can also be included in a single mixing element such as a coil, a helical element or a turbine-shaped element like an impact baffle. A further example of a plurality of geometric elements is a plurality of helical elements. A well-known helical mixing element—in this case a static mixer—is the Kenics® mixer, which consists of a series of alternating left and right hand helical elements. Other examples of installations that all destroy the secondary flow pattern of the process fluid are a grid, intersecting blades and/or other shaping elements. For sake of clarity defined that that the term "installation" as used herein is understood to exclude bends e.g. the bends of a coiled flow inverter.

A installation achieves mixing by means of flow splitting and flow redirection, including possibly flow inversion, and thus achieves motionless mixing. An installation typically contains a series of geometric elements that can for instance be screw-shaped, lamellar (including chequered fins) or lattice-shaped. The geometric elements can be taken to define baffles. Each of the geometric elements can be envisaged to divide a laminar product stream, skew portions of the current and rejoin them. In addition, radial mixing effects usually participate in the overall mixing. An installation can also contain or be defined by branching of a tube into a plurality of channels that are recombined to a single tube.

According to a first aspect, there is disclosed a unit operation formed by a device. The unit operation is a device and comprises a helical flow inverter. The unit operation formed by a device can be part of a modular product plant i.e. a modular system for the continuous, microbe-reduced production and/or processing of a product solution.

The helical flow inverter has a single inlet at one end and an outlet at the opposite end. The helical flow inverter further comprises at least one installations. As already noted above, the installation is distinct from a bend of an angle from 45° to 180°, but fulfils the same functionality. Within each helical flow inverter at least one, preferably several installation are implemented, transforming the helix into a helical flow inverter (HFI). Thus, as used herein the term "helical flow inverter" (HFI) refers to a helical tube comprising at least one installation, and wherein the length of the HFI tubing in total has to be adequate to ensure a residence time of each portion of the product stream which is sufficient for viral inactivation. It should be noted that the residence time decreases in a HFI compared to a helical tube without installations. In contrast as used herein the term "CFI" used as acronym for coiled flow inverter refers to a device with plurality of coils linked by bends at a certain angle, typically in the range from 45° to 180°.

A person skilled in the art knows how to determine, whether a residence time of each portion of the product stream which is sufficient for viral inactivation. For example, it can be determined whether viral particles are present at defined point along the helical tube.

This determination can be carried out for example using standard methods known in the art such as next generation sequencing and/or other PCR-based methods in combination with sequencing methods. Moreover, quantification of the viral particles is possible. In general, virus quantification involves counting the number of viruses in a specific volume to determine the virus concentration via methods such as plaques assay, focus forming assay, endpoint titration—also termed endpoint dilution assay—protein-based virus quantification assays, transmission electron microscopy, tunable resistive pulse sensing, quantitative PCR and/or large volume plating.

The installation can for example contain a helical element and/or a plurality of baffles. The installation can in some embodiments contain a nozzle or a contraction choke. The installation can in some embodiments contain a plurality of fluid flow channels and/or a tube with a circumferential wall having a plurality of indentations.

In some embodiments of the unit operation formed by a device the unit operation formed by a device comprises more than one HFI comprising said installations, i.e. more than one HFI. This is especially the case, if the dimensions of a single HFI would be too large for a given facility and thus two or more HFIs are arranged in series. It should be noted, that also in such an embodiment the total tube length of all HFIs of a given unit operation formed by a device taken together has to be sufficient to ensure sufficient viral inactivation. This is the case as in such an embodiment the more than one HFI define a single conduit and are thus arranged in series. Linking elements are interposed between the HFIs.

In contrast to a CFI, the axis of the HFI can be in parallel to the direction of gravity. As gas bubbles rise upwards this enables easy deaeration. If a unit operation formed by a device comprises more than one HFI and the inlet is at the bottom, the outlet of the first HFI is preferably connected to the bottom inlet of the second HFI with a conduit guaranteeing high flow velocity to move bubbles downward. In one embodiment of this aspect at least one installations are comprised into the linking elements.

A HFI can be of any desired material that is suitable for the desired application. Generally, under the intended conditions of flow and solution used, the HFI is of fixed diameter rather than of expandable nature. Within this precondition, the degree of softness/stiffness of the tube walls can be selected as desired. In some embodiments the HFI can for example be defined by a flexible tubing. In some embodiments the HFI is defined by a pipe. In some embodiments the HFI is defined by a hose. Typically, but not restricted to, each HFI in a given unit operation formed by a device is made of the same material as each other HFIs included in the same unit operation formed by a device. In some embodiments different HFIs of the unit operation formed by a device can be made of material of different softness/stiffness.

In some embodiments, the inlet and the outlet of the HFI, or if a unit operation formed by a device comprises more than one HFI, the inlet into the first HFI and the outlet of the last HFI are capable of fluidly communicating with a conduit for routing a liquid product or a product solution. In some embodiments the inlet and the outlet of the at least one HFIs are in fluid communication with a conduit for routing a liquid product or a product solution of a product formation apparatus. The inlet and the outlet of the at least one HFIs can be connected to portions of a respective conduit. In some embodiments the at least one HFIs can be integrated, for instance as a connecting portion, into a respective conduit for routing a liquid product or a product solution.

In some embodiments of the unit operation formed by a device, at least one HFIs are designed to be capable of allowing a process fluid to flow continuously through it. A respective process fluid can be or contain a liquid product. A process fluid can in some embodiments be an aqueous solution, for example of a macromolecule. A respective macromolecule can for example be a polypeptide/protein, a nucleic acid, and/or a polysaccharide. In some embodiments the process fluid is a solution, generally an aqueous solution, of an antibody. It is possible to use the HFI in both laminar and turbulent flow conditions, laminar flow conditions are preferred.

As explained above, laminar flow is characterized by a fast-moving center of the tube, e.g. the pipe. The Reynolds number is known to depend on the dimensions of a tube, in particular its diameter.

The Dean number is a dimensionless characteristic that describes the flow of a fluid in a curved channel or pipe. It is defined as $$Dn = \frac{Re}{\sqrt{\lambda}}$$

In this definition, u is the mean flow velocity in the tube, v is the dynamic viscosity of the fluid, s is the distance between the curved surfaces, in particular the diameter of the pipe or channel, and r is the radius of curvature.

Using the Reynolds number Re, the following expression can be formulated:

$$Re = \frac{\rho \cdot u \cdot d_i}{\eta}$$

The Dean number is therefore the product of the Reynolds number (based on axial flow through a pipe of the diameter and the square root of the curvature ratio. The Dean number is a characteristic for determining whether perturbations are formed in curved channels by the divertion of the fluid flow. The Dean number is therefore a critical characteristic that determines whether a certain design of a unit operation formed by a device is suitable for achieving a required residence time distribution under the desired conditions. As can be taken from the above expressions, a parameter that can conveniently be adjusted for a given design is the flow velocity.

In some embodiments the unit operation formed by a device has a Dean number number ≥1, preferably ≥2, more preferably ≥3, most preferably between 3 and 100.

The modified torsion parameter T* on the other hand describes the effect of Re number and the geometry on the tightness of the RTD and is calculated according to:

$$T = \frac{\pi \cdot r_c \cdot Re}{p}$$

In some embodiments the unit operation formed by a device as a torsion parameter of ≥0, also have a torsion parameter ≥100, ≥200, ≥300, ≥400, particularly preferably between 500 and 10000.

The conduit for routing a liquid product or a product solution can be a tubing. The respective conduit can for example be a pipe or a flexible hose. However, it is also possible to generate a unit operation formed by a device in which the conduit for routing a liquid product or a product solution is formed by a fixed outer structure with a hollow center allowing for routing of a liquid product or a product solution, e.g. a structure printed via a 3D printing technology.

In some embodiments the unit operation formed by a device further comprises a conditioning element. As used herein the term "conditioning element" refers to a device which generates the conditions for viral inactivation. This is for instance achieved via mixing or adjusting the pH to below pH 4 or by adding a solvent or a detergent etc. The conditioning element is or includes in some embodiments a container capable of releasing an acidic solution or a solution containing an solvent and/or a detergent for viral inactivating purposes or a caustic solution for viral inactivation into the at least one HFI. A caustic solution can for example be an alkaline solution. In some embodiments the conditioning element is a homogenization loop. This is especially preferred if the process fluid enters the unit operation formed by a device continuously and if the unit operation formed by a device prior to the unit operation formed by a device described herein is a bind and elute chromatography. In this setting the homogenization loop ensures that the process fluid enters the HFI at a predetermined and constant pH e.g. pH 4.

In embodiments where the operation contains at least two HFIs a first HFI can have an axis h and a second HFI can have an axis h', and the HFIs are connected by a linking element, which connects the outlet of the first HFI to the second HFI. In a preferred embodiment the first HFI with an axis h and a HFI with an axis h' are of the same length/height in the direction of their respective axis h or h', so that the axes h and h' are of the same length.

In some embodiments the linking element can comprise both at least one installation and a non-helical tube. In some embodiments the unit operation formed by a device includes at least one sensor. The at least one sensor can for example be selected form the group consisting of: pH Sensor, UV Detector, conductivity sensor and temperature sensor. The sensor can be arranged within the at least one HFIs. The sensor can also be arranged at a position outside the at least one HFIs for example within a conduit for routing a process fluid that is coupled to the at least one HFIs. In some embodiments the sensor can also be arranged at a position within a conduit for routing a process fluid that is upstream the inlet of at least one HFI. In some embodiments the sensor can also be arranged at a position within a conduit for routing a process fluid that is downstream the inlet of at least one HFIs. In some embodiments in which the unit operation formed by a device comprises more than one sensor sensors can also be arranged at a position within a conduit for routing a process fluid that is upstream and/or downstream the inlet of at least one HFI.

The terms "upstream" and "downstream" in this regard refer to the flow of a process fluid through the at least one HFI of a given unit operation formed by a device as described herein, when the unit operation formed by a device comprising the HFI itself is in between two other unit operation formed by a devices of a conduit for routing a process fluid. The portion of the conduit through which the process fluid flows prior to entering the Unit operation formed by a device comprising the HFI is referred to as upstream. The portion of the conduit through which the process fluid flows after having passed through the unit operation formed by a device comprising the HFI is referred to as downstream the HFI.

As noted above, in some embodiments of the unit operation formed by a device at least one HFIs have an axis h that is arranged at an angle between 0° and 90° relative to the direction of gravitation. In some embodiments the axis h can thus be arranged at least essentially in the direction of gravitation. This arrangement has the advantage that it facilitates de-aeration. i.e. the removal of gas bubbles. If gas bubbles are not removed, they can—via disturbing flow patterns—affect the residence time distribution of a HFI. In extreme cases gas bubbles can partly prevent the fluid stream—comprising the desired product—from passing a unit operation formed by a device such as filtration and/or can prevent the normal conduction of a given unit operation formed by a device such as a chromatography to a significant extend. Hence, gas bubbles should be removed. In some embodiments the axis h can be inclined relative to the direction of gravitation. In some of these embodiments the respective HFI can be positioned in a frame, which can be carried by a holding rack. Overall, the virus-inactivation device comprising at least one HFI, i.e. the unit operation formed by a device offers the superior scalability (improved removal of air at larger tube diameters) of a simple straight helix in combination with the superior residence time characteristics of the CFI.

In some embodiments all elements/components of the unit operation formed by a device coming into contact with the process liquid or process fluid are made of sanitizable material. The respective material can be sterilisable and/or sanitizable in that it can be exposed to heat and/or steam. As an example, the material can be capable of standing exposure to a temperature of 160-190° C. for a period of e.g. 10 minutes to two hours. The material can for example be capable of standing exposure to steam at a temperature of 121-134° C. under enhanced pressure such as 100 kPa. Exposure times that the material can stand can be 30 minutes, one hour or more. In some embodiments all elements/components of the unit operation formed by a device coming into contact with the process liquid or process fluid are made of autoclavable material. The respective material can also be sterilisable and/or sanitizable in that it can be exposed to irradiation, for example UV radiation. The respective material can also be sterilisable by exposure to electron beam processing or gamma radiation. In some embodiments all elements/components of the unit operation formed by a device are made of gamma-sterilisable material. A respective material can also be sterilisable and/or sanitizable by exposure to X-ray radiation. In some embodiments all elements/components of the unit operation formed by a device coming into contact with the process liquid or process fluid are made of material that is capable of standing exposure to ethylenoxide, typically for an extended period of time. A respective material can for instance be capable of standing exposure to ethylenoxide for a period of 60 hours. In some embodiments all elements/components of the unit operation formed by a device coming into contact with the process liquid or process fluid are made of material that is capable of standing exposure to NaOH, generally in the form of a solution of NaOH of 0.5 M or more, such as 1 M NaOH or more.

In some embodiments at least one HFIs of the unit operation formed by a device have an inner diameter in the range from 1 to 50 mm, preferably 2 to 30 mm, most preferably 3-15.

Typically, the unit operation formed by a device is of such a capacity that it is capable of inactivating virus particles due to providing a predetermined residence time under virus inactivating conditions. Usually capacity of the unit operation formed by a device is suitable to allow adequate inactivation of sufficient virus particles that may be included in a process fluid. A container capable of releasing an acidic solution into the line for routing a process fluid is for example of a size that allows releasing sufficient acidic solution to achieve a pH value of ≤4 in a continuous flow of the product or the product solution for a desired period of time.

The unit operation formed by a device described herein can include a support rack carrying at least one frames. In some embodiments the support rack is positioned at the axis of the helix of a HFI. The support rack and/or the at least one frame can be hollow, filled or solid. If a HFI is of sufficient strength and stiffness the HFI can also be provided in the form of a self-supporting structure.

The unit operation formed by a device can be designed and dimensioned as explained in WO 2015/135844. Bends of a certain angle, also explained in WO 2015/135844, are nevertheless not required in a unit operation formed by a device disclosed herein, instead the HFI comprises installations as described above and in case the unit operation formed by a device comprises several HFIs these are connecting by a linking element as described above.

The total length and the inner diameter of the at least one HFI is chosen according to the particular space available and according to the dimensions of the overall plant. The design of the at least one HFI including the tube length and the tube diameter, will furthermore be chosen according to the flow rate of the plant in such a manner that the residence times required for a particular application are maintained.

As an illustrative example, the length of at least one, including all, HFIs can be chosen in the range from 1 to 200 m, or 50 to 500 m. In some embodiments the length of at least one, including all, HFIs can be in the range from 10 to 100 m.

The number of turns in between of two installations of the at least one HFI of the unit operation formed by a device can in some embodiment be chosen to be in the range from 0.5 to 20, preferably 3 to 15, most preferably 9-11. It should be noted that the residence time decreases in a HFI compared to a helical tube without installations.

The narrow residence time distribution achieved using a unit operation formed by a device as disclosed herein allows achieving the required virus inactivation at a certain product-dependent and process-dependent minimal residence time. In doing so it minimizes the maximum residence time, without reaching the maximum contact time which is also product- and process-dependent. Reaching the maximum contact time would lead to unacceptable damage to the product. The required minimum as well as the maximum residence time are product-dependent and are typically determined experimentally. The maximum residence time is optimized so that a product contained in a process fluid suffers as little damage as possible, in order to minimize the need for subsequent purification steps. The HFI approximates the residence time distribution of an ideal plug flow tube reactor. This ensures effective, continuous inactivation of virus particles at low pH values in parallel to minimal product damage. In some embodiments the unit operation formed by a device is included in modular product plant i.e. a modular system for the continuous, microbe-reduced production and/or processing of a product solution or a liquid product. As used herein, the term "modular" means that the individual steps of the process carried out by the modular system for the continuous, microbe-reduced production and/or processing of a product solution or a liquid product can be carried out in separate modules that are connected to one another, the modules being preconfigured and microbe-reduced and it being possible to connect them to one another in a closed manner and in different combinations. In the context of the invention, the term "modular system" means a series of modules ("units/unit operations formed by devices") in which a fluid ("product stream/process fluid") can be conveyed and which are connected to one another for carrying out at least two downstream and/or upstream steps, in which a fluid ("product stream/process fluid") can be conveyed. In this connection, the individual modules of the "modular system" can be connected to one another in any combination. Examples of modules in the context of the invention are inter alia the unit operation formed by a device for viral inactivation described herein comprising at least one HFI as well as a filtration module, a chromatography module, an ultrafiltration module, a diafiltration module and a dialysis module.

The at least one HFI of a given unit operation formed by a device, i.e. in the case of more than one HFIs all HFIs, taken together comprise 2-100 installations, preferably 20-80 and most preferably 40-60 installations.

A person skilled in the art knows that apart from using acidic solution or a solution containing an solvent and/or a detergent for viral inactivating purposes or a caustic solution for viral inactivation as mentioned above another way of carrying out continuous virus inactivation is irradiation with UV-C light. Thus, in addition or as alternative to the other virus inactivation methods mentioned above a radiation source can be arranged in a position relative to at least a portion of the HFI. Said radiation source is of such a power that it is capable of exposing the process fluid to enough UV-C light that virus particles present within the HFI described herein are inactivated. Again the narrow residence time distribution achieved in the at least one HFI tube (HFI) disclosed herein allows achieving the required time for virus inactivation under continuous conditions at a certain product-dependent and process-dependent minimal residence time.

In some embodiments the unit operation formed by a device is a virus-inactivation device. A respective virus-inactivation device can be a conditioning device in combination with the at least one HFI described herein according to the second aspect. Any of the following explanations can thus also apply to the unit operation formed by a device according to the first aspect, and vice versa, unless a statement would clearly contradict the explanations on the respective other aspect.

According to a second aspect, there is disclosed the use of the unit operation formed by a device according to the first aspect for virus inactivation of a flow of a process fluid. Typically the use of the unit operation formed by a device for virus inactivation is for continuous virus inactivation of a continuous flow of a process fluid. The use includes providing a continuous flow of the process fluid to be inactivated. The use furthermore includes feeding the continuous flow of the process fluid into the inlet of the at least one HFI of the unit operation formed by a device. The use also includes allowing passage of the flow of the process fluid through the at least one HFI of the unit operation formed by a device. When the process fluid flows through the at least HFI of the unit operation formed by a device the use includes exposing the process fluid to conditions of virus inactivation. As a result, the process fluid is allowed to be virus-inactivated. The use also includes allowing outflow of the stream of the virus-inactivated process fluid from the at least one HFI of the unit operation formed by a device via the outlet.

In some embodiments exposing the process fluid to conditions of virus inactivation includes exposing the process fluid to an acidic pH value, such as a pH value of ≤4. In some embodiments exposing the process fluid to conditions of virus inactivation includes an adjustment of the pH of the stream of the process fluid to a value of ≤4, if the pH value of the process fluid to be inactivated is >4. In some embodiments adjusting the pH value includes contacting the process fluid with a solution of an acid such as acetic acid or caprylic acid. In some embodiments the use can include determining the pH value of the process fluid to be inactivated. If the pH value is determined to be >4, an acidic solution can be allowed to contact the process fluid. In some embodiments the use can include determining the pH value of the process fluid to be inactivated after an acidic solution has been allowed to contact the process fluid.

In some embodiments exposing the process fluid to conditions of virus inactivation includes exposing the process fluid to a solvent and/or a detergent.

In some embodiments exposing the process fluid to conditions of virus inactivation includes mixing the process fluid in a homogenization loop. This is especially preferred if the process fluid enters the unit operation formed by a device continuously and if the unit operation formed by a device prior to the unit operation formed by a device or the virus inactivation device described herein is a bind and elute chromatography. In this setting the homogenization loop ensures that the process fluid enters the HFI at a predetermined and constant pH e.g. a pH 4 as condition of virus inactivation.

In some embodiments exposing the process fluid to conditions of virus inactivation includes exposing the process fluid to a caustic solution, for example an alkaline solution. In some embodiments exposing the process fluid to conditions of virus inactivation includes allowing an alkaline or otherwise caustic solution to be introduced into the process fluid.

As explained above, the unit operation formed by a device in some embodiments contains a conditioning element. Exposing the process fluid to conditions of virus inactivation can include activating the respective conditioning element.

The process fluid is usually a liquid. The process fluid generally is or contains a liquid product or a product solution. In some embodiments the product to be inactivated is a solution or a suspension of peptides or macromolecules, see also above. In some embodiments a respective macromolecule is a protein, such as an immunoglobulin or a hormone. A respective protein can also be a growth factor.

In addition, it should be noted that in order to increase the output of the modular production plant comprising the unit operation formed by a device described herein, the flow rate ca be increased. As the residence time of the unit operation formed by a device described herein needs to match the minimum time required for viral inactivation, two or more unit operations formed by devices as described herein can be used in parallel to increase the output.

BRIEF DESCRIPTION OF THE DRAWINGS

The skilled artisan will understand that the drawings, described below, are for illustration purposes only. The drawings are not intended to limit the scope of the present teachings or claims in any way.

DEFINITIONS

Figure 1:
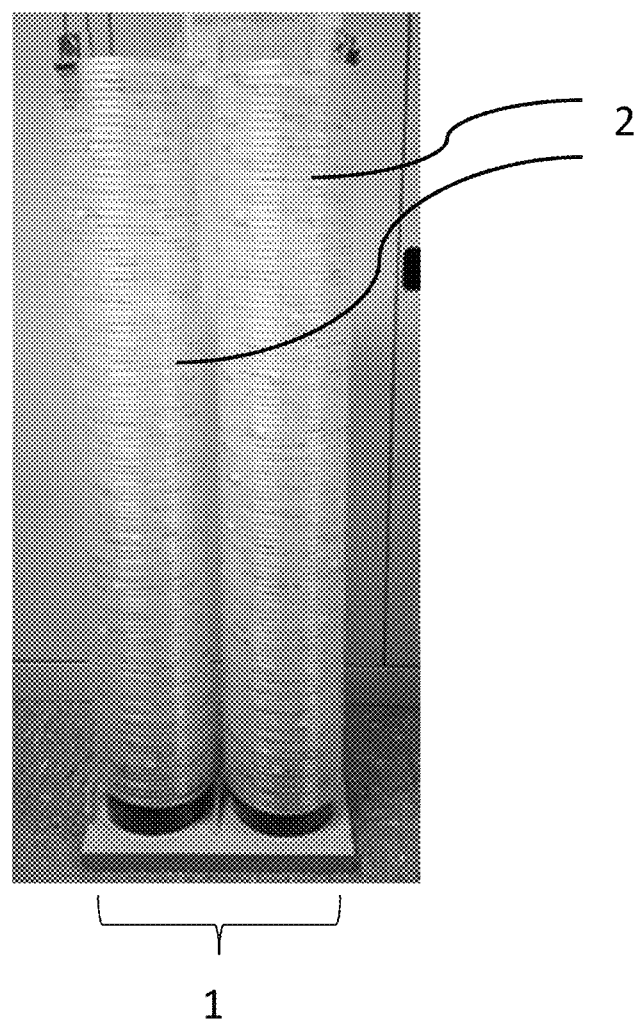
FIG. 1 depicts a photograph of a unit (1) operation comprising two HFIs (2) as described herein with the following dimensions: inner tube diameter 6.4 mm, coil tube diameter 0.2 m, number of installations for each HFI 40, height of each HFI 130 cm.
Figure 2:
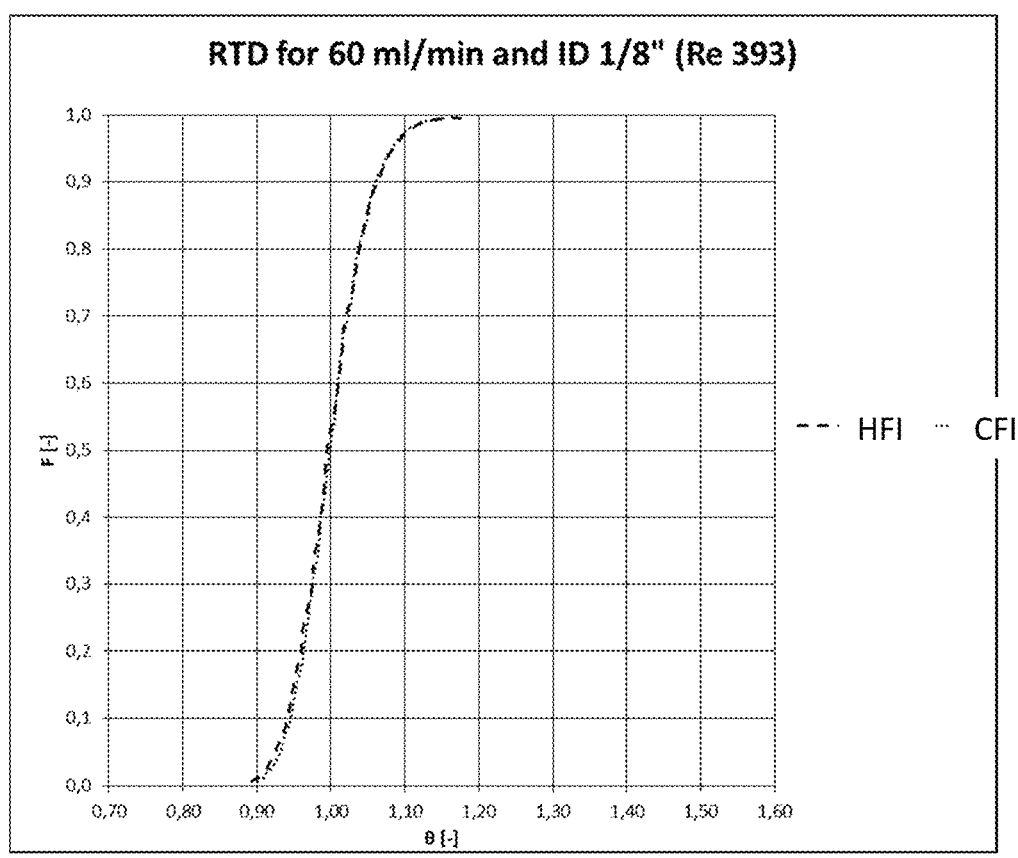
FIG. 2 shows the residence time distribution of a unit operation formed by a device with a HFI featuring 39 installations, as disclosed herein, in comparison to a unit operation formed by a device with a coiled flow inverter as disclosed in WO 2015/135844 The tube diameter was chosen to be 3.2 mm (1/8"), and the flow rate was set to 60 ml/min. The helical flow inverter had a Reynolds number of >50, a Dean number of >9 and a torsion parameter. It can be clearly seen that the behaviour of the CFI and HFI are very close to each other, showing a very tight residence time distribution. Thus, the HFI can be used for a process scale up without compromising on residence time distribution. As a conclusion the HFI offers the superior scalability (improved removal of air at larger tube diameters) of a simple straight helix in combination with the superior RTD characteristics of the CFI.

Unless stated otherwise in the above, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system.

The term "essentially consists of" is understood to allow the presence of additional components in a sample or a composition that do not affect the properties of the sample or a composition. As an illustrative example, a pharmaceutical composition can include excipients if it essentially consists of an active ingredient.

The terms "comprising", "including," containing", "having" etc. shall be read expansively or open-ended and without limitation. Singular forms such as "a", "an" or "the" include plural references unless the context clearly indicates otherwise. Thus, for example, reference to a "tube" includes a single tube as well as a plurality of tubes. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

As used herein, the term "continuous" refers to the fact that the input of the components to be processed and/or a process fluid into a unit e.g. the unit operation formed by the device described herein and the removal of the processed components and/or the product stream from said unit, take place without interruption. In other words, a subsequent unit operation can start processing the product fluid before a first unit operation has finished processing the product fluid.

As used herein the term "homogenization loop" refers to a piece of tubing, which allows the process fluid to be circulated e.g. pumped in said piece of tubing until a desired characteristic is reached. For example, the piece of tubing is circular and the process fluid is pumped around said circle until a pH value of <4 is reached.

The listing or discussion of a previously published document in this specification should not necessarily be taken as an acknowledgement that the document is part of the state of the art or is common general knowledge.

EXAMPLES

Materials and Methods

Liquids

Ultrapure water is provided by the water treatment system Milli-Q® Direct by Merck Millipore (Billerica, USA) and is filled into a 30 L plastic barrel from the company MAUSER (Brühl, Germany) For conductivity measurements, a solution of 1 M NaCl is prepared by dissolving crystalline NaCl from Sigma-Aldrich (St. Louis, USA) in Milli-Q® water, which is stored in a 30 L plastic barrel (MAUSER).

Hoses

All hoses are obtained from the company Saint Gobain Performance Plastics (Charny, France). The hoses used are C-Flex 374 biopharmaceutical tubing (3.2 mm and 6.4 mm ID) and PharMED BPT biopharmaceutical tubing (3.2 mm ID). Straight connectors obtained from the company Nordson Medical (Loveland, USA) serve as connecting pieces.

Degassing Module

MicroModule® degassing modules from Liqui-Cel Membrana (Charlotte, USA) are used for the in-line degassing of the liquids.

Pump

The pump is a Masterflex® L/S hose pump with an easy-load II pumphead by Cole-Parmer (Wertheim, Germany).

Analysis

For an analysis of the residence time behaviour, the conductivity is measured and recorded.

Conductivity Measurements

Conductivity is measured using PendoTECH (Princeton, USA) single-use conductivity sensors (CONDS-N-25). For data recording, the sensors are connected to the Pressure-MAT™ Plus (PendoTECH) program via a CMONT conductivity monitor on a commercially available laptop.

What is claimed is:

1. A unit operation formed by a device for providing a narrow residence time comprising a single inlet at one end and an outlet at the opposite end and a helical tube comprising at least one installation characterized by at least one of a plurality of geometric elements thereby forming a helical flow inverter or HFI, wherein the at least one installation characterized by at least one of a plurality of geometric elements of the HFI is a device for mixing fluids that does not require an actuated element, but achieves mixing by making use of fluid mechanics, and wherein the unit operation does not require a bend.

2. The unit operation formed by a device according to claim 1, comprising at least two HFIs interconnected in series by at least one linking element.

3. The unit operation formed by a device according to claim 1, wherein the unit operation further comprises a conditioning element, wherein the conditioning element is selected from
   (i) a container capable of releasing an acidic solution or a solution containing a solvent or detergent for viral inactivating purposes or a caustic solution for viral inactivation into the HFI and/or
   (ii) a homogenization loop.

4. The unit operation formed by a device according to claim 1, wherein the HFI is designed to be capable of allowing a process fluid to flow continuously through the HFI.

5. The unit operation formed by a device according to claim 1, wherein the unit operation is made from disposable material.

6. The unit operation formed by a device according to claim 1, wherein the HFI has a Dean number from 3 to 100 and/or modified Torsion number between 500 and 10000.

7. The unit operation formed by a device according to claim 1, wherein the installations characterized by at least one of a plurality of geometric elements comprises at least one of a helical element, a plurality of baffles, a contraction choke, a plurality of fluid flow channels, and/or a tube with a circumferential wall having a plurality of indentations.

8. The unit operation formed by a device according to claim 1, wherein the at least one HFI has an axis h that is arranged in an angle between 0° and 90° relative to the direction of gravitation, and wherein the at least one HFI is positioned in at least one frames carried by a holding rack.

9. The unit operation formed by a device according to claim 1, wherein at least all elements of the unit operation coming into contact with the process fluid are made of disposable and/or sterilisable and/or sanitizable material, wherein the sterilisable and/or sanitizable material optionally is capable of withstanding exposure to autoclavation, to gamma-irradiation, to ethylenoxide and/or NaOH.

* * * * *

UNITED STATES PATENT AND TRADEMARK OFFICE
CERTIFICATE OF CORRECTION

PATENT NO. : 11,786,615 B2
APPLICATION NO. : 16/772068
DATED : October 17, 2023
INVENTOR(S) : Lobedann et al.

It is certified that error appears in the above-identified patent and that said Letters Patent is hereby corrected as shown below:

In the Specification

In Column 5, Line 33, delete "(based" and insert -- based --, therefor.
In Column 5, Line 36, delete "divertion" and insert -- diversion --, therefor.
In Column 6, Line 33, delete "form" and insert -- from --, therefor.
In Column 10, Line 47, delete "ca be" and insert -- can be --, therefor.

In the Claims

In Column 14, Line 2, in Claim 7, delete "installations" and insert -- installation --, therefor.

Signed and Sealed this
Fifth Day of March, 2024

Katherine Kelly Vidal
Director of the United States Patent and Trademark Office